United States Patent
Clarke et al.

(10) Patent No.: US 10,357,798 B2
(45) Date of Patent: Jul. 23, 2019

(54) VAPOR SHEATH FOR LIQUID DISPENSING NOZZLE

(71) Applicant: GlaxoSmithKline LLC, Philadelphia, PA (US)

(72) Inventors: Allan J. Clarke, Philadelphia, PA (US); Frederick H. Fiesser, King of Prussia, PA (US); James A. McHugh, Landsdowne, PA (US)

(73) Assignee: GLAXOSMITHKLINE LLC, Philadelphia, PA (US)

( * ) Notice: Subject to any disclaimer, the term of this patent is extended or adjusted under 35 U.S.C. 154(b) by 0 days.

(21) Appl. No.: 14/663,609

(22) Filed: Mar. 20, 2015

(65) Prior Publication Data

US 2015/0190834 A1    Jul. 9, 2015

Related U.S. Application Data

(60) Continuation of application No. 13/389,457, filed on Feb. 8, 2012, now Pat. No. 8,986,777, which is a division of application No. 12/854,566, filed on Aug. 11, 2010, now Pat. No. 8,967,074.

(60) Provisional application No. 61/232,898, filed on Aug. 11, 2009.

(51) Int. Cl.
*B05B 15/50* (2018.01)
*B05B 15/55* (2018.01)
*B05D 1/02* (2006.01)
*A61M 11/00* (2006.01)

(52) U.S. Cl.
CPC .............. *B05D 1/02* (2013.01); *B05B 15/50* (2018.02); *B05B 15/55* (2018.02); *A61M 11/00* (2013.01)

(58) Field of Classification Search
CPC .............................. B05B 15/02; B05B 15/025
USPC ........ 118/302; 134/104.1–104.3; 347/22–36; 239/110, 112
See application file for complete search history.

(56) References Cited

U.S. PATENT DOCUMENTS

| | | | |
|---|---|---|---|
| 3,134,544 A | 5/1964 | Copkey | |
| 4,387,002 A | 7/1983 | Knecht | |
| 5,075,047 A | 12/1991 | Youngeberg | |
| 5,435,488 A * | 7/1995 | Abiko | B05B 1/302 134/104.1 |
| 2008/0100685 A1* | 5/2008 | Otis | B05D 1/26 347/100 |

FOREIGN PATENT DOCUMENTS

| JP | H0729789 A | 1/1995 |
|---|---|---|
| JP | 3137808 | 12/2007 |

OTHER PUBLICATIONS

English Translation JP2507966, Jun. 19, 1996.*

(Continued)

*Primary Examiner* — Yewebdar T Tadesse
(74) *Attorney, Agent, or Firm* — Ohlandt, Greeley, Ruggiero & Perle, LLP

(57) ABSTRACT

The present disclosure provides a device for preventing the fouling of a liquid dispensing nozzle. The end of the dispensing nozzle is placed in a hollow interior of a band carrying the same solvent that is dispensed by the nozzle. The solvent on the band evaporates into a gap between the band and the dispensing nozzle, thus providing a vapor sheath, or environment in the gap, that helps to prevent the fouling of the dispensing nozzle.

11 Claims, 6 Drawing Sheets

(56) References Cited

OTHER PUBLICATIONS

Israel Office Action (with English translation) dated Jan. 29, 2015 for Israel application No. 217921.
Korean Office Action (with English translation) dated Jun. 9, 2017 for Korean application No. 10-2012-7006240.

* cited by examiner

VAPOR SHEATH FOR LIQUID DISPENSING NOZZLE

CROSS-REFERENCE TO RELATED APPLICATIONS

The present application is a continuation of U.S. patent application Ser. No. 13/389,457, filed on Feb. 8, 2012, which will issue on Mar. 24, 2015 as U.S. Pat. No. 8,986,777 which, in turn, is a divisional of U.S. patent application Ser. No. 12/854,566, filed on Aug. 11, 2010, which issued on Mar. 3, 2015, as U.S. Pat. No. 8,967,074, and both of which claim priority to U.S. Provisional Patent Application No. 61/232,898, filed on Aug. 11, 2009.

BACKGROUND OF THE DISCLOSURE

1. Field of the Disclosure

The present disclosure relates to a device for improving the dispensing of fluids from a nozzle or similar device. In particular, the present disclosure relates to a device that creates a sheath of solvent vapor in the vicinity of the dispensing end of the nozzle to prevent the fouling or clogging of the nozzle by materials deposited on the nozzle end as a result of solvent evaporation.

2. Description of the Related Art

In the art of fluid dispensing technology, it is often required to dispense a material that is dissolved in a carrier solvent. There are many environmental circumstances that can cause evaporation of the carrier solvent. This can create an undesirable situation, because when the carrier solvent evaporates, solid material can form at the end of the dispensing nozzle. This solid material fouls or clogs the nozzle. Thus, there is a need for a device to overcome this problem.

SUMMARY OF THE DISCLOSURE

The present disclosure provides a device for a fluid dispensing nozzle that prevents or minimizes the evaporation of a solvent in the vicinity of the nozzle end.

The present disclosure provides a porous or solid band that can be placed around the end of the dispensing nozzle. The fluid in the dispensing nozzle comprises the ingredient that is to be delivered to the target (for example, in a pharmaceutical application, the active agent), and one or more carrier solvents. The same carrier solvent or carrier solvents that are present in the fluid being dispensed through the nozzle are supplied to the band in the manner described below. A situation is created where the band is saturated, or nearly so, with the same solvent or solvents within the dispensing nozzle, so that it creates a sheath of vapor in the local environment around the nozzle end. The vapor sheath can be at the nozzle end, and/or can surround the dispensing end of the nozzle. The vapor sheath has been found to prevent the evaporation of the solvent at the nozzle end, thus preventing the clogging or fouling of the nozzle.

Thus, in one embodiment, the present disclosure provides a device for dispensing a fluid onto a target. The device comprises a dispensing nozzle having an end for emitting the fluid onto the target, wherein the fluid comprises a solvent. The device further comprises a band having a hollow interior and an inner surface. The band is positioned so that the end of the dispensing nozzle is in the hollow interior, and so that a gap is formed between the inner surface of the band and the end of the dispensing nozzle. The band also has the solvent present thereon. The solvent present on the band evaporates into the gap to assist in the prevention of evaporation of the solvent at said end of the dispensing nozzle.

DETAILED DESCRIPTION OF THE DISCLOSURE

Figure 1:
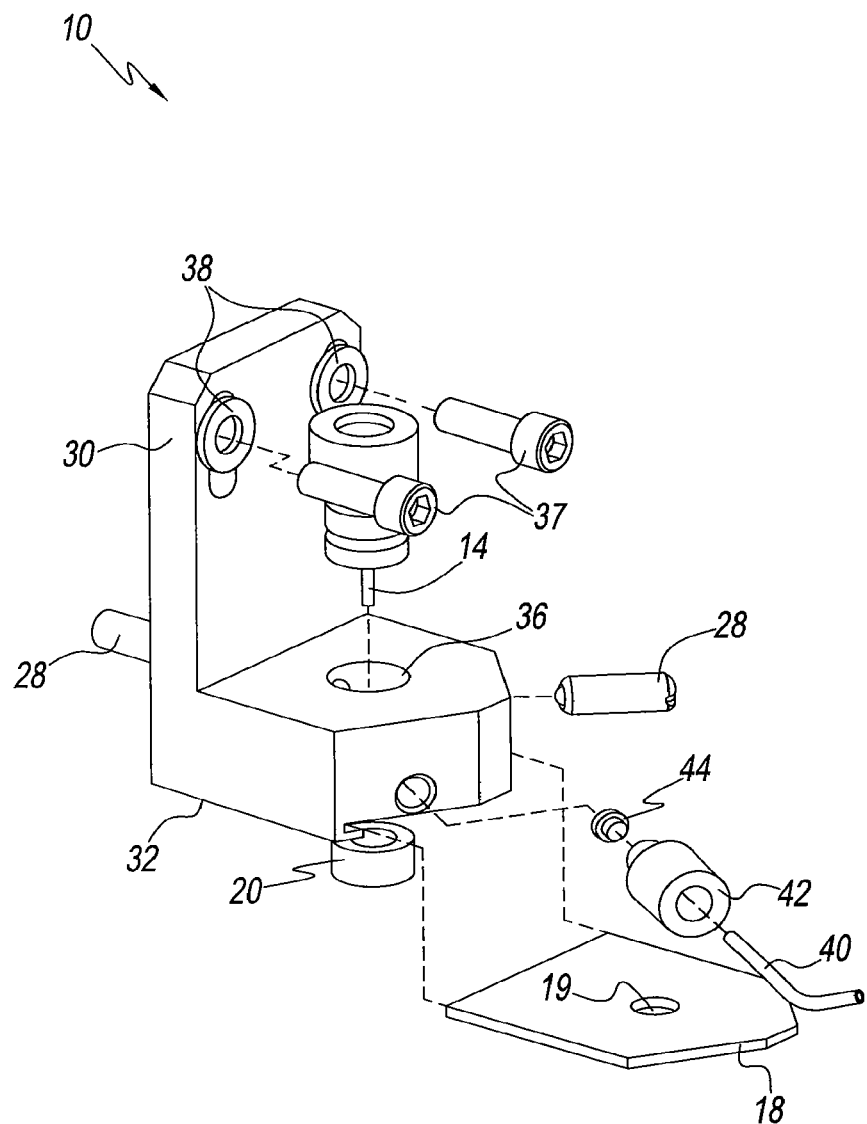
FIG. 1 shows an exploded view of the dispensing nozzle mount assembly of the present disclosure.

Referring to the Figures, dispensing nozzle mount assembly 10 is shown. Assembly 10 comprises nozzle 12, and band 20. Band 20 has a hollow interior 21, and an inner surface 22. As shown and as described in greater detail below, nozzle 12 is placed in the top end of a hole 36 through mount 30, and band 20 is mounted in a counterbore at the bottom end of hole 36, so that an end 14 of nozzle 12 is in hollow interior 21. A gap 25 is thus formed between end 14 of dispensing nozzle 12 and inner surface 22. A fluid (not shown), which comprises one or more solvents, and usually at least one other ingredient, such as a pharmaceutical active or a polymer, is dispensed through nozzle 12, and out the bottom 32 of mount 30, onto a target (not shown).

Band 20 is saturated with the same solvent or solvents that are dispensed through nozzle 12, in liquid form, and in the manner discussed below. The solvent(s) are replenished as necessary in order to keep band 20 at the desired level of saturation with the solvent(s). Without being bound by any theory, it is believed that liquid solvent(s) present on or in band 20 evaporate(s) into the gap 25 between inner surface 22 and end 14 of nozzle 12, thus maintaining a higher vapor concentration of the solvent(s) in gap 25. This helps to prevent evaporation of the solvent(s) within nozzle 12, which helps to prevent the clogging or fouling problem discussed above. Thus, with a very simple and inexpensive device, the present disclosure has improved the efficiency of dispensing nozzles.

Figure 4:
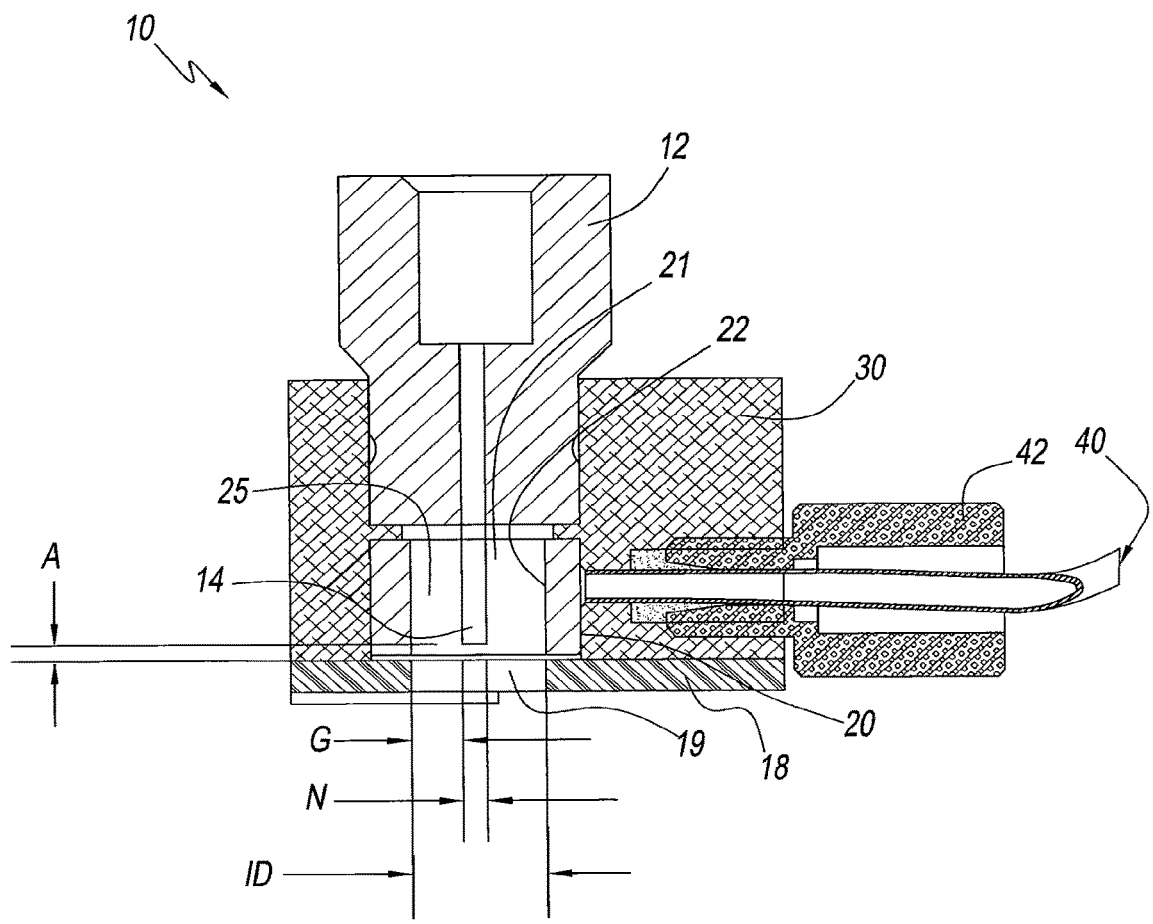
FIG. 4 is a cross-sectional view of the dispensing nozzle mount assembly taken along line 4-4 of FIG. 3.

As shown in FIG. 4, end 14 of nozzle 12 preferably does not extend below a top surface of drip gasket 18 (discussed in further detail below), and should remain within hollow interior 21 of band 20. This will help to ensure that the vapor pressure of the solvent within gap 25 will prevent the fouling of nozzle 12. However, the present disclosure also contemplates embodiments in which end 14 does in fact extend into hole 19 of drip gasket 18.

Band 20 can be made of any porous material that is suitable for holding a solvent in the manner described above, at the desired level of saturation. In one embodiment, especially for pharmaceutical applications, band 20 is made of a porous plastic material, such as polypropylene (PP) or polytetrafluoroethylene (PTFE). Other suitable polymers include ultra-high molecular weight polyethylene (UHMWPE), high-density polyethylene (HDPE), and polyvinylidene fluoride (PVDF), ethylene vinyl acetate (EVA), nylon-6, polyurethane (PE) and PE/PP Co-polymer. These polymers can be purchased from the Porex Corporation.

The type of material suitable for a particular application will depend on the solvent being dispensed by nozzle 12. For example, if the solvent is alcohol or acetone, PTFE may be particularly suitable. The plastic may be porous or sintered, so that the solvent is deposited on the outer surface 23 of band 20 in the manner discussed below, and migrates to the inner surface 21 of band 20, via the pores throughout band 20. At any given time, the solvent may be present on inner surface 22, outer surface 23, or a combination thereof. If the plastic is porous, it can have a porosity ranging from 20% to 80%, or any sub-ranges in between.

In another embodiment, the material of band 20 does not have to be porous at all, as long as it is able to hold the solvent in the desired manner, i.e. by creating the desired vapor concentration in gap 25. For example, a solid (i.e., non-porous) material having a high surface roughness on at least inner surface 22 may be able to keep enough solvent on inner surface 22, so that band 20 would remain wet, and allow solvent to evaporate into gap 25.

Although in many applications, such as those involving pharmaceutical actives, band 20 will often need to be made of a plastic material, the present disclosure contemplates other materials for band 20. For example, band 20 can be made of a metal or fibrous material that can also be also porous, or sintered.

Figure 5:
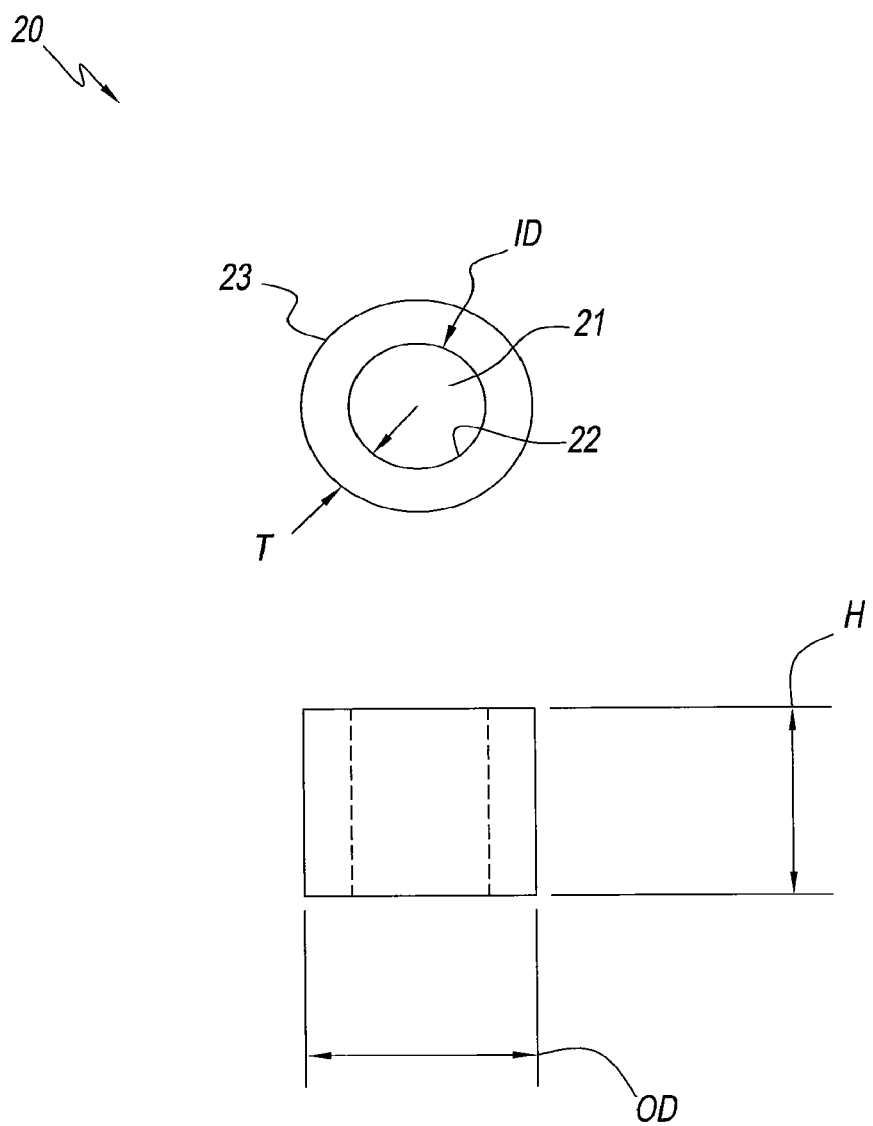
FIG. 5 shows a top and side view of the band of the present disclosure.

In the shown embodiment, band 20 is a circular, porous annular ring. Referring specifically to FIGS. 4 and 5, band 20 can have an outer diameter OD, which can correspond to the diameter of the hole 36 in mount 30 through which nozzle 12 is placed. In one embodiment, the outer diameter OD can be about 0.336" to about 0.372" (inches), or precisely 0.336" to 0.372", +/−0.005" at either end of that range. Band 20 can also have an inner diameter ID, which can be about 0.217" to about 0.218", or precisely 0.217" to 0.218"+/−0.005" at either end of that range. Band 20 can have a height H of about 0.236" to about 0.32", or precisely 0.236" to 0.32", +/−0.01" at either end of that range. The annular thickness T can be about 0.077" or precisely 0.077"+/−0.005". The end 14 of nozzle 12 can have a diameter N of about 0.050", or precisely 0.050"+/−0.005". End 14 of nozzle 12 can be at a height A above the top surface of drip gasket 18, which can be about 0.024" above the top surface of drip gasket 18, or precisely 0.024"+/−0.005".

The gap 25 between the inside diameter of band 20 and nozzle 12 should be appropriately sized, so that the vapor pressure of the solvent or vapor environment in gap 25 is enough to prevent the solvent in nozzle 12 or at the end 14 of nozzle 12 from evaporating, as discussed above. In one embodiment, gap 25 can be a distance G of about 0.084", or precisely 0.084"+/−0.005", measured from the end 14 of nozzle 12 to an inner surface of band 20. As used in the present specification, the term "about" with respect to dimensional characteristics means the recited number, give or take measurement tolerances. The dimensions discussed above can also be the exact amounts—for example, gap 25 can be exactly 0.084", or band 20 can have a height H of exactly 0.32".

It should be emphasized that the above-described dimensions are only for particular embodiments, and that any number of sizes of band 20 will provide the functionality and features described in the present disclosure. The appropriate dimensions relating to band 20 and gap 25 will depend on the amount and type of solvent used, and the size of nozzle 12, among other factors. In addition, although in the shown embodiment band 20 is a circular, annular ring that has a constant inner diameter ID, outer diameter OD, and thickness T, the present disclosure contemplates other annular shapes for band 20, such as oval, square, rectangular, elliptical, or any other shape that can provide the required vapor pressure in gap 25.

Referring again to FIGS. 1, 2, and 4, assembly 20 can have a drip gasket 18 connected to the bottom 32 of mount 30, below nozzle 12 and band 20. The drip gasket 18 can catch any overflow of solvent falling or dripping off of band 20. This helps to prevent any extra solvent from falling onto the target substrate. In addition, drip gasket 18 can provide a larger surface of evaporation for the solvent, thus keeping the target free of excess solvent and possibly contributing to the vapor pressure of the solvent in gap 25. Referring to FIGS. 1 and 4, drip gasket 18 can have a hole 19 disposed therein that corresponds to the end 14 of nozzle 12, so that the fluid leaving nozzle 12 and traveling to the target substrate can pass through drip gasket 18. In some embodiments, it may be necessary to have a gap or distance between the bottom surface of band 20 and the top surface of drip gasket 18. This will prevent drip gasket 18 from wicking away solvent from band 20. The gap can be seen in FIG. 4.

Figure 2:
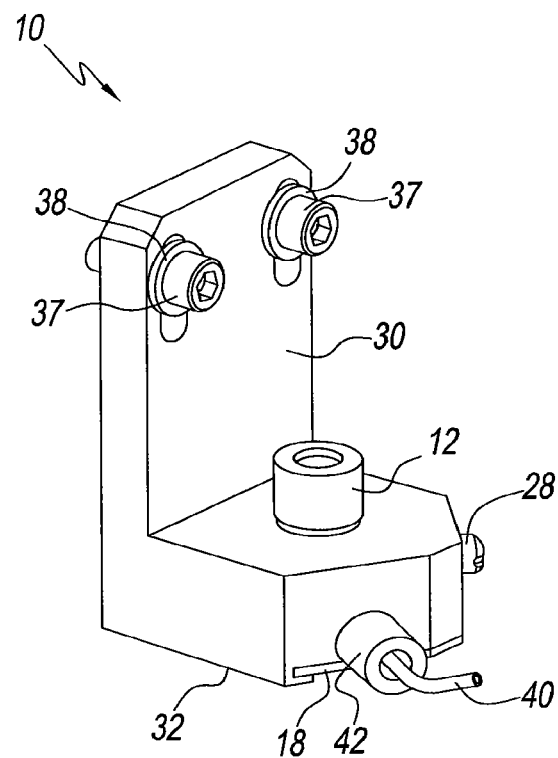
FIG. 2 shows a perspective view of the dispensing nozzle mount assembly of FIG. 1, fully assembled.

Referring to FIGS. 1, 2, and 4, assembly 10 can also comprise solvent feeder tube 40 that can be connected to mount 30 with nut 42 and ferrule 44. Tube 40 can be in fluid communication with a supply of the solvent (not shown) to ensure that band 20 stays loaded with the desired amount of solvent. Solvent can be fed by tube 40 to outer surface 23 of band 20 with a continuous flow process, or intermittent flow process, or through a device (not shown) that delivers solvent to band 20 at scheduled intervals. In one embodiment, solvent is supplied to band 20 through tube 40 at a rate of 10-20 uL/min. Although, in the case of porous bands, it is preferred and easier to add the solvent to outer surface 23, the present disclosure contemplates adding the solvent to inner surface of 22 of band 20 as well.

Figure 3:
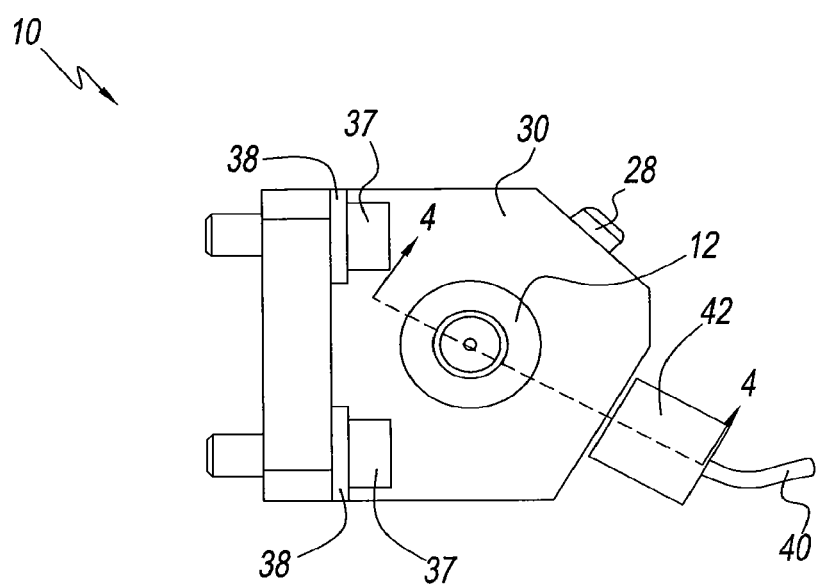
FIG. 3 is a top view of the dispensing nozzle mount assembly of FIG. 2.

When in use, band 20 is placed in the bottom 32 of mount 30, in hole 36 as shown in FIG. 1. Nozzle 12 can be secured in place with one or more plungers 28. Referring to FIG. 3, mount 30 can be connected to another component of a machine with one or more bolts or fasteners 37 and washers 38. Nozzle 12 can then be connected to a source of dispensing fluid (not shown), for use in the desired application.

Figure 6:
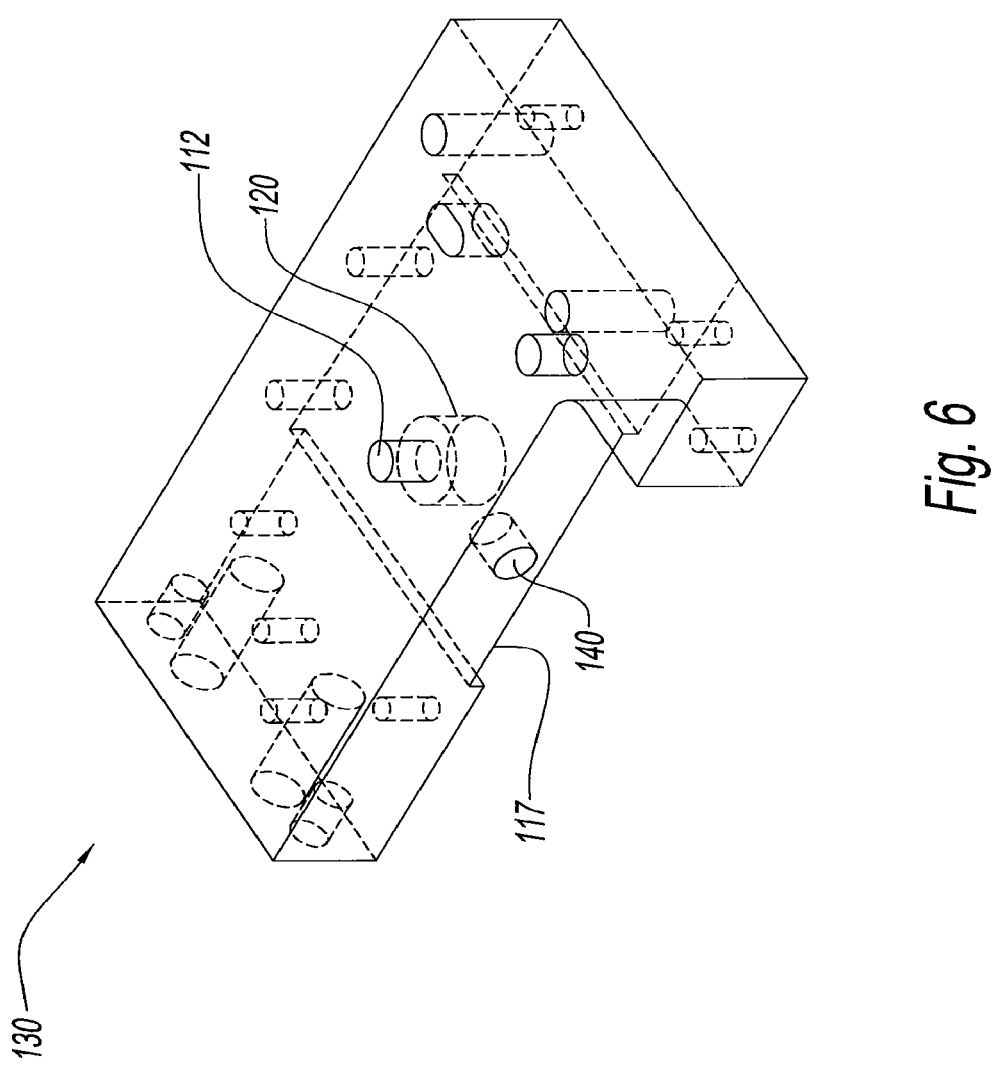
FIG. 6 shows a second embodiment of a mount for the dispensing nozzle mount assembly of the present disclosure.
Figure 7:
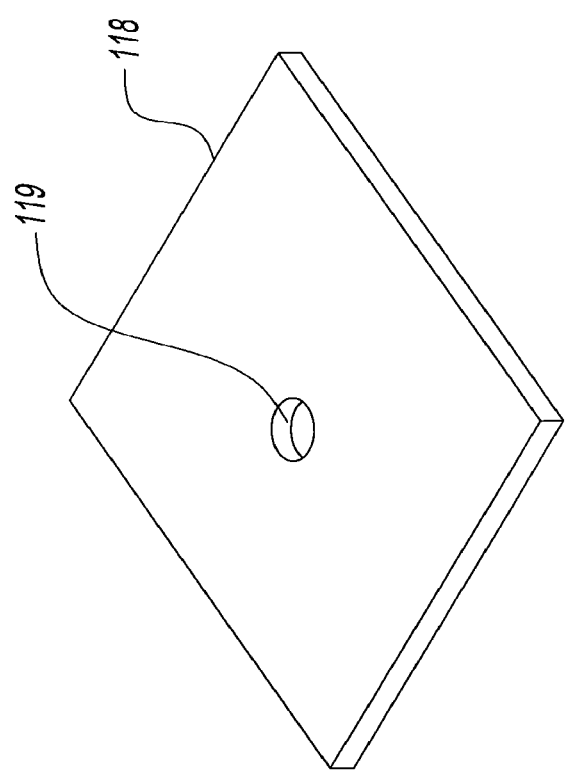
FIG. 7 shows a drip gasket for the mount of FIG. 6.

Referring to FIGS. 6 and 7, an alternate design of mount 30 is shown, and referenced by numeral 130. Mount 130 has dispensing opening 112 on a top surface thereof, through which end 14 of dispenser 12 can be placed. Band 20 can be placed in recess 120, located in a bottom surface of mount 130. Mount 130 also has a solvent dispensing opening 140 located on the side, through which solvent is fed to band 20. Drip gasket 118 has a shape (as shown in FIG. 7, this can be square) that matches a gasket depression 117 in the bottom of mount 130, and is connected to mount 130 in this manner. Drip gasket 118 is connected to mount 130 so that gasket hole 119 corresponds to dispensing opening 112 and the inner diameter of band 20, as described above with respect to mount 30. Aside from the above-described features, the embodiment of assembly 10 using mount 130 works in the same fashion as described above with respect to mount 30.

Assembly 10 can be used in any number of applications where it is desired to apply a fluid to a target, such as pharmaceuticals, food processing applications, or electronic device applications. The target for the dispensed fluid can be any number of surfaces, such as but not limited to metal, plastic, glass, wood, or a food product. The target can also be a substrate used in a pharmaceutical application, such as a tablet, caplet, capsule, or vial tray. The target can also be a material used in an electronic application, such as a circuit board. The target can also be an open container, such as a vial. The target can also be a diagnostic or medical device.

In addition to, or instead of the liquid solvent supplied to band 20, a flow of solvent vapor can be pumped or otherwise delivered to an area around nozzle 12. This supply of vapor will function in largely the same way as the vapor evaporating from band 20, i.e. to provide a sufficient vapor environment around nozzle 12 to prevent the evaporation of solvent on or within nozzle 12. In any embodiment provided the appropriate safety measures are taken, heat could be used to enhance solvent evaporation.

The present disclosure having been thus described with particular reference to certain embodiments thereof, it will be obvious that various changes and modifications may be made therein without departing from the spirit and scope of the present disclosure.

What is claimed is:

1. A device for dispensing a fluid onto a target, comprising:

a dispensing nozzle having an end for emitting the fluid onto the target, wherein the fluid comprises an amount of a carrier solvent;

an annular band having a height, an upper opening and a lower opening, wherein the annular band is a non-porous material having a hollow interior and an inner surface, wherein the inner surface has a constant dimension along the height from the upper opening to the lower opening, wherein the inner surface has an additional amount of the same carrier solvent thereon, wherein the inner surface has a surface roughness sufficient to retain the additional amount of the carrier solvent thereon, wherein the non-porous annular band is positioned so that the end of the dispensing nozzle is in the hollow interior to form a gap between the inner surface of the non-porous annular band and the end of the dispensing nozzle, and wherein the additional amount of the carrier solvent retained on the inner surface evaporates into the gap to provide a vapor sheath around the dispensing nozzle to assist in the prevention of evaporation of the amount of the carrier solvent in the fluid at the end of the dispensing nozzle; and a drip gasket comprising a planar structure disposed below both the end of the nozzle and the bottom opening of the non-porous annular band, wherein the drip gasket has an opening therethrough disposed and configured to align with the end of the nozzle and the bottom opening of the non-porous annular band.

2. The device of claim 1, wherein the non-porous annular band is a circular band having a constant outer diameter and annular thickness.

3. The device of claim 1, wherein the non-porous annular band is made of a plastic material.

4. The device of claim 3, wherein the plastic material is a polymer.

5. The device of claim 4, wherein the polymer is selected from the group consisting of polypropylene, polytetrafluoroethylene, ultra-high molecular weight polyethylene, high-density polyethylene, polypropylene, polyvinylidene fluoride, ethylene vinyl acetate, nylon-6, polyurethane, polyethylene/polypropylene co-polymer, and any combinations thereof.

6. The device of claim 5, wherein the polymer is selected from the group consisting of polypropylene, polytetrafluoroethylene, and a combination thereof.

7. The device of claim 1, further comprising a mount for holding the dispensing nozzle, the non-porous annular band and the drip gasket.

8. The device of claim 7, wherein the mount has a hole therethrough with a top opening and a bottom opening, and wherein the dispensing nozzle is in the top opening, and the non-porous annular band is in the bottom opening of the hole.

9. The device of claim 8, wherein the mount further comprises a bottom surface, and wherein the drip gasket is connected to the bottom surface, and wherein the drip gasket is disposed and configured to catch an overflow of the additional amount of the carrier solvent from the non-porous annular band.

10. The device of claim 1, wherein the non-porous annular band has a shape selected from the group consisting of oval, square, rectangular, and elliptical.

11. The device of claim 1, further comprising a heat source for applying heat to assist in the evaporation of the additional amount of the carrier solvent from the non-porous annular band.

* * * * *